United States Patent
Wang

(10) Patent No.: US 9,931,030 B2
(45) Date of Patent: Apr. 3, 2018

(54) ENDOSCOPE DEFOGGING AND PRE-HEATING DEVICE

(71) Applicant: Wei-Hsun Wang, New Taipei (TW)

(72) Inventor: Ching-Chuan Wang, New Taipei (TW)

(73) Assignee: Wei-Hsun Wang, New Taipei (TW)

( * ) Notice: Subject to any disclaimer, the term of this patent is extended or adjusted under 35 U.S.C. 154(b) by 435 days.

(21) Appl. No.: 14/736,236

(22) Filed: Jun. 10, 2015

(65) Prior Publication Data

US 2015/0282699 A1 Oct. 8, 2015

Related U.S. Application Data

(63) Continuation-in-part of application No. 12/508,561, filed on Jul. 23, 2009, now abandoned.

(51) Int. Cl.
*H05B 6/64* (2006.01)
*A61B 1/12* (2006.01)
*F24J 3/00* (2006.01)
*A61B 1/253* (2006.01)
*A61B 50/00* (2016.01)

(52) U.S. Cl.
CPC .............. *A61B 1/127* (2013.01); *A61B 1/128* (2013.01); *F24J 3/003* (2013.01); *A61B 1/253* (2013.01); *A61B 2050/0016* (2016.02)

(58) Field of Classification Search
CPC .......... A61B 1/127; A61B 1/128; A61B 1/253; A61B 2050/0016
USPC ........ 219/756, 759, 761, 763, 212; 126/247, 126/263.03, 263.01, 204; 607/108; 600/182; 165/100
See application file for complete search history.

(56) References Cited

U.S. PATENT DOCUMENTS

| 5,205,278 A | 4/1993 | Wang | |
|---|---|---|---|
| 2007/0157921 A1* | 7/2007 | Rankin | C09K 5/18 126/263.01 |
| 2014/0114128 A1* | 4/2014 | Wills | A61B 1/00105 600/114 |

* cited by examiner

*Primary Examiner* — Quang Van
(74) *Attorney, Agent, or Firm* — Guice Patents PLLC

(57) ABSTRACT

An endoscope defogging and pre-heating device includes a bag including a first seal line and first and second chambers defined at an opposite lateral sides relative to the first seal line, a heat storage/release material flowing between the first chamber and the second chamber for storing/releasing heat energy, a fixation device for securing the bag in a folded status to hold the endoscope to be pre-heated between the first and second chambers, and an actuator bendable to generate oscillation waves for causing the heat storage/release material to produce a temperature rise and then to release heat for pre-heating the loaded endoscope to about 98° F.~138° F.

10 Claims, 8 Drawing Sheets

ENDOSCOPE DEFOGGING AND PRE-HEATING DEVICE

BACKGROUND OF THE INVENTION

1. Field of the Invention

The present invention relates to means for pre-heating endoscopes and more particularly, to an endoscope defogging and pre-heating device based on the technical features of U.S. Pat. No. 5,205,278. The endoscope defogging and pre-heating device uses a fixation device to hold a bag in a folded condition for pre-heating endoscopes efficiently.

2. Description of the Related Art

Heat storage/release devices are known for years for use to keep the body warm or for the purpose of cold compress. There are many methods to prepare heat storage/release devices. Conventionally, a water bladder may be used to hold hot water for keeping the body warm. There is also known a hot compress bag that comprises a bag body filled with a fluid and sealed, and a metal actuator strip mounted in the bag body and operable to actuate the fluid, causing a chemical reaction and release of heat. During heat producing and releasing procedure, the hot compress bag provides heat energy for hot compress application. U.S. Pat. No. 5,205,278, issued to the present inventor, discloses a similar design, entitled "Heat storage/release device for hot/cold compress application", which comprises a bag, which defines therein a sealed accommodation space, a heat storage/release material, which is accommodated in the accommodation space of the bag and adapted for storing/releasing heat energy, and flexible members fastened to the bag at two opposite sides relative to the accommodation space and bendable to hold the bag in a predetermined shape and to secure the bag to a person's face.

Further, following fast development of technology, many endoscopes have been created and are intensively used to look inside a body cavity or organ. Before application, the endoscope must be pre-heated, performing primary sterilization and reducing patient's discomfort.

Before using endoscopes, the lenses of the endoscopes must be wiped with an anti-fogging agent, for example, but not limited to, Devon® FOG-OUT® #3910, to prevent lens fogging to interfere with optical clarity due to changes in temperature.

Nowadays, steam heaters and heat storage/release devices are commonly used for pre-heating endoscopes. FIG. 1 illustrates an endoscope pre-heating device according to the prior art. According to this prior design, the endoscope pre-heating device comprises a heater 100 defining therein a water bath 110, a plastic sheeting 111 covering the heater 100 over the surface of the water bath 110 to hold water in the water bath 100. In application, the endoscopes 160 to be pre-heated are put in water in the water bath 110 above the plastic sheeting 111, and then the heater 100 is started up to heat water and the endoscopes 160.

Thus, it does not necessary to wipe the lenses of endoscopes with an anti-fogging agent when using the aforesaid endoscope pre-heating device to pre-heat endoscopes, avoiding chemical residues in the body of the patient. However, this prior art design of endoscope pre-heating device requires much installation space and needs to consume electricity. Further, if water in the water bath 110 is not well sterilized, it can cause bacterial infections in the patient.

FIG. 2 illustrates another design of endoscope pre-heating device according to the prior art. According to this design, the endoscope pre-heating device comprises a heating tube 200 and a power adapter 210. The heating tube 200 has mounted therein an electric heating wire or thermoelectric coupling (not shown). In application, put the endoscope 160 to be pre-heated in the heating tube 200, and then turn on the heating tube 200 to heat the endoscope 160.

This prior art design of endoscope pre-heating device still has drawbacks as follows:

1. The electric heating wire or thermoelectric coupling of the heating tube 200 must be electrically conducted for heating the endoscope 160, however, the heating temperature of the electric heating wire or thermoelectric coupling is not controllable, and the patient can be scalded by the endoscope 160 if the heating temperature is excessively high.

2. An external power source is needed.

3. It needs power adapter 210.

4. The inner diameter of the heating tube 200 is not adjustable to fit different endoscopes of different sizes, and thus, the heating efficiency will be low if the heating tube 200 cannot positively surround the loaded endoscope.

Therefore, there is need for an endoscope defogging and pre-heating device that eliminates the aforesaid drawbacks.

SUMMARY OF THE INVENTION

The present invention has been accomplished under the circumstances in view. It is one object of the present invention to provide an endoscope defogging and pre-heating device, which uses a fixation device to hold a bag in a folded status for pre-heating an endoscope to about 98° F.~138° F.

It is one object of the present invention to provide an endoscope defogging and pre-heating device, which has a first chamber and a second chamber defined in a bag at two opposite lateral sides relative to at least one first seal line so that the first chamber and the second chamber can be kept in close contact with the endoscope to be pre-headed after the bag is folded up, enhancing endoscope pre-heating efficiency.

To achieve these and other objects of the present invention, an endoscope defogging and pre-heating device comprises a bag, a heat storage/release material, a fixation device, and an actuator. The bag comprises at least one first seal line, a first chamber defined at one lateral side relative to the at least one first seal line, and a second chamber defined at an opposite lateral side relative to the at least one first seal line. The heat storage/release material is accommodated in the bag and flowing in the first chamber and the second chamber and adapted for storing/releasing heat energy. The fixation device is mounted at two opposite lateral sides of the bag, and adapted for securing the bag in a folded status for surrounding an endoscope with the first chamber and the second chamber. The actuator is mounted in the bag, and bendable to generate oscillation waves for causing the heat storage/release material to produce a temperature rise and then to release heat for pre-heating an endoscope to a temperature range about 98° F.~138° F.

Other advantages and features of the present invention will be fully understood by reference to the following specification in conjunction with the accompanying drawings, in which like reference signs denote like components of structure.

DETAILED DESCRIPTION OF THE PREFERRED EMBODIMENT

Figure 1:
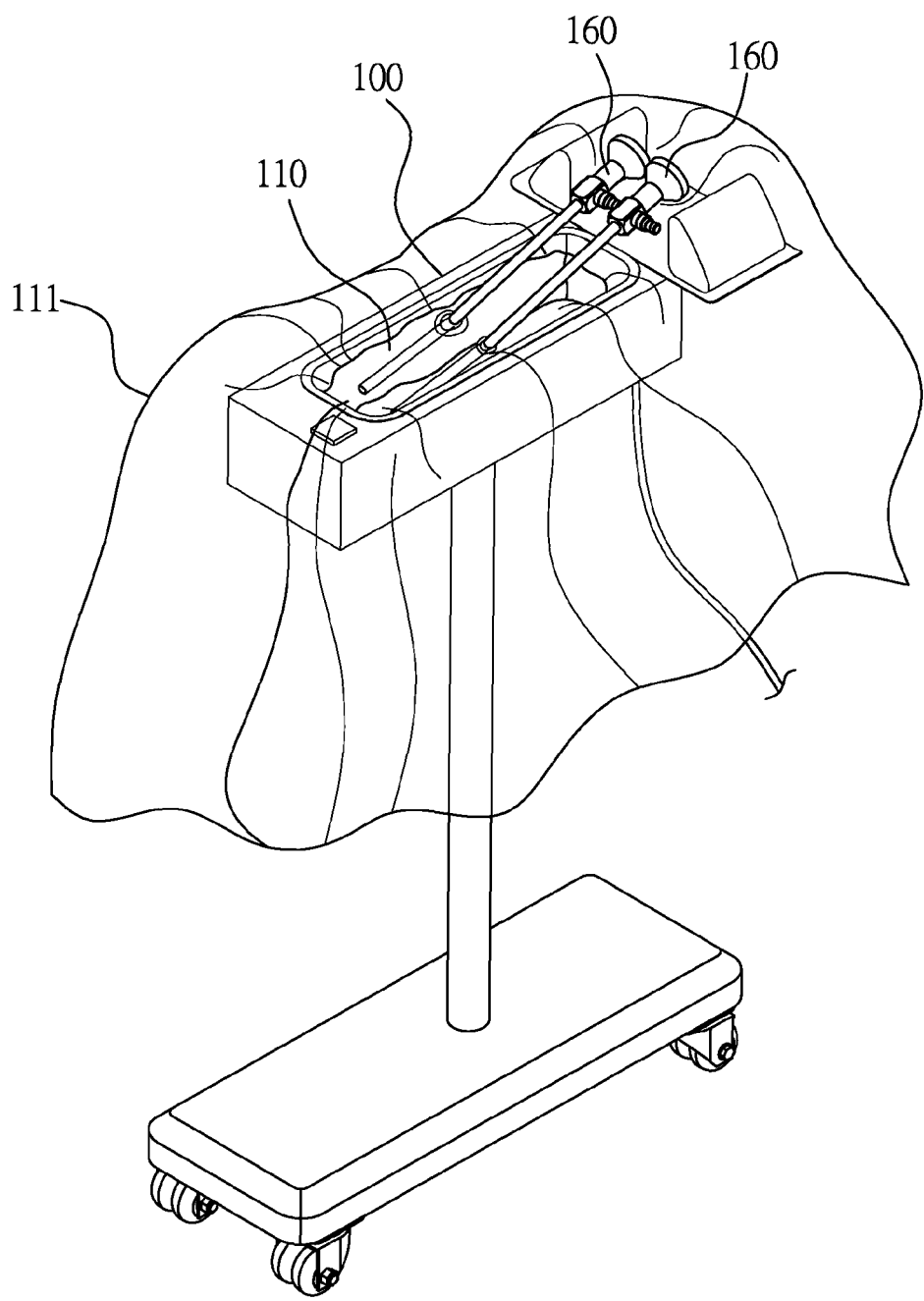
FIG. 1 is a schematic drawing illustrating an endoscope pre-heating device according to the prior art.
Figure 2:
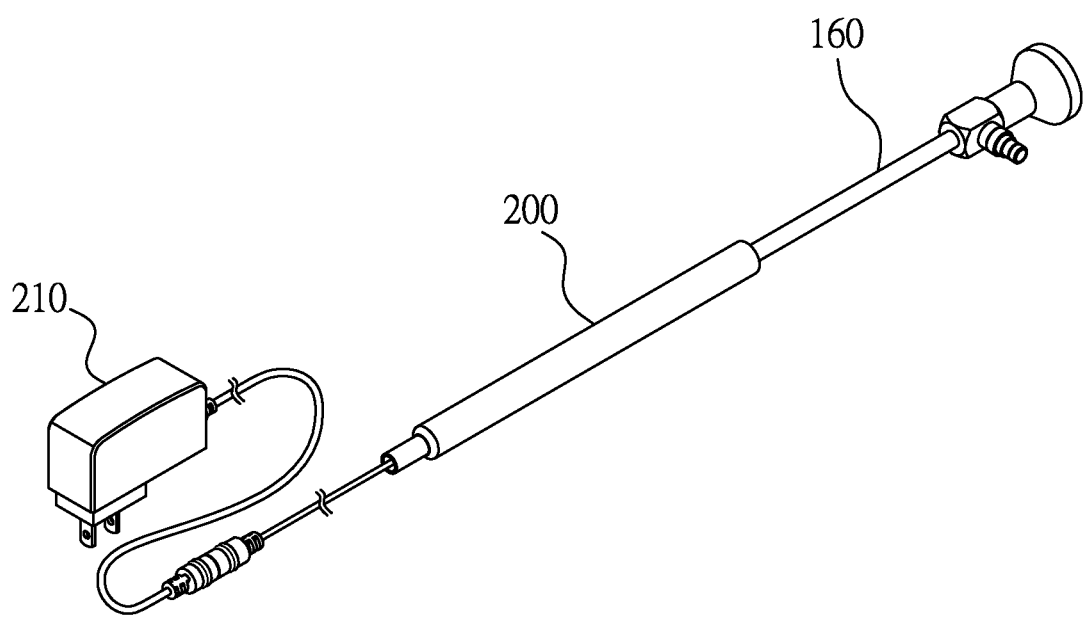
FIG. 2 is a schematic drawing illustrating another design of endoscope pre-heating device according to the prior art.
Figure 3:
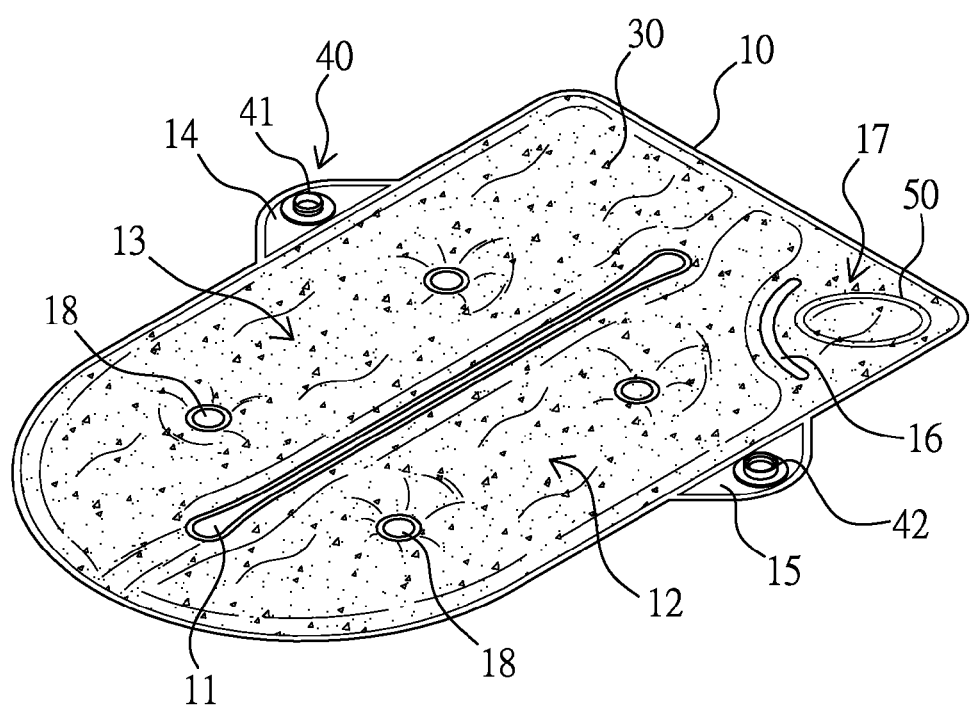
FIG. 3 is an extended view of an endoscope defogging and pre-heating device according to the present invention.
Figure 4:
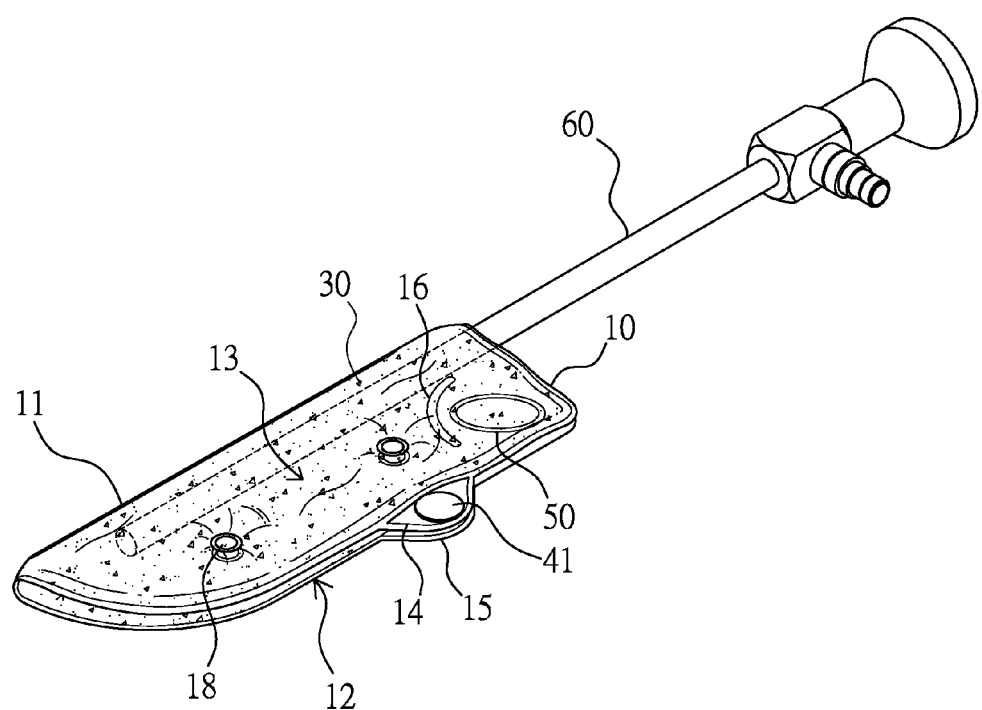
FIG. 4 is a schematic applied view of the present invention, illustrating the endoscope defogging and pre-heating device folded up with an endoscope set in between the first chamber and second chamber of the bag.
Figure 5:
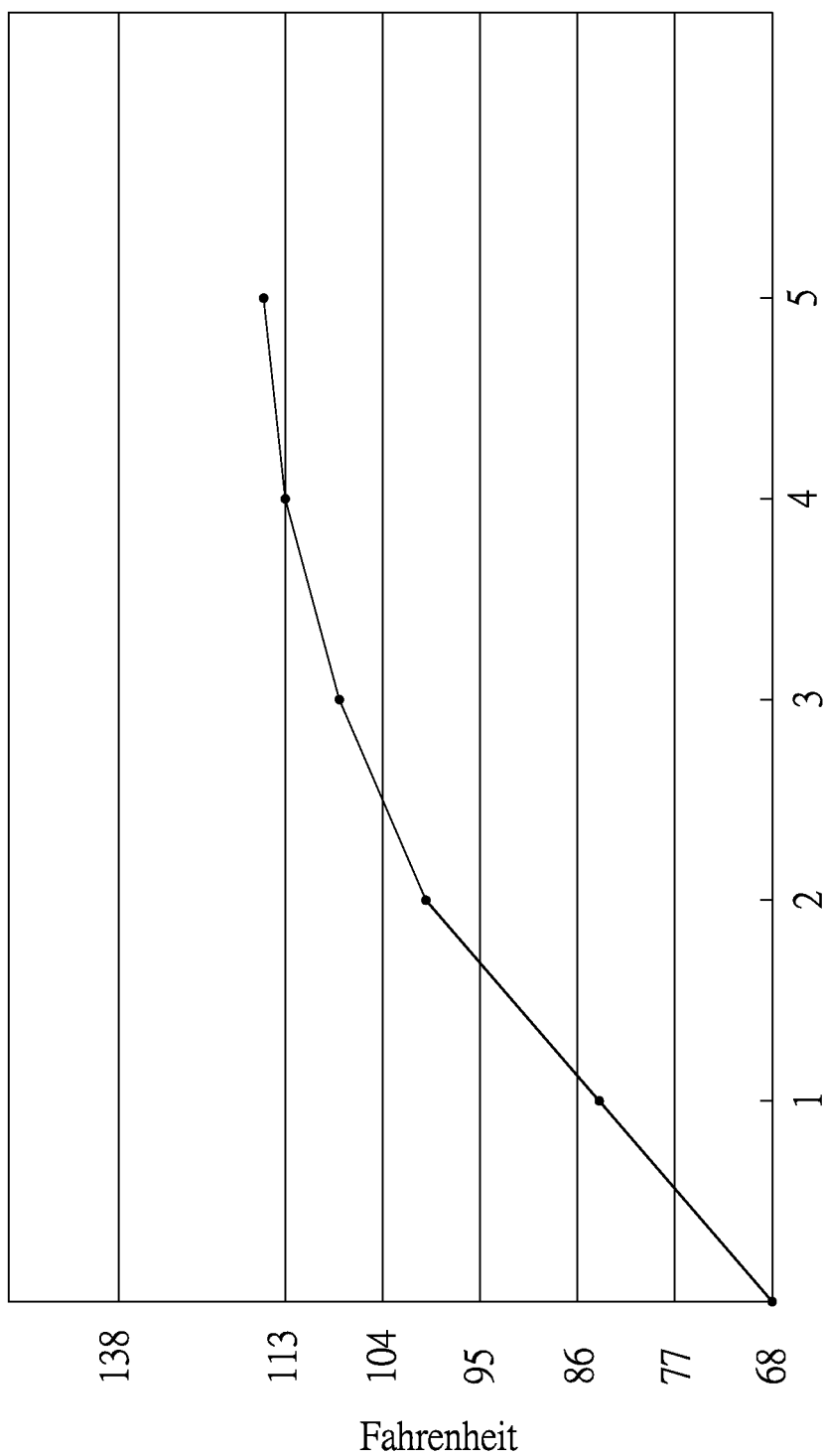
FIG. 5 is a time-temperature curve, illustrating temperature changes in the endoscope at different time periods under the pre-heating operation of the endoscope defogging and pre-heating device.

Referring first to FIGS. 3-5 where FIG. 3 is an extended view of an endoscope defogging and pre-heating device according to the present invention; FIG. 4 is a schematic applied view of the present invention, illustrating the endoscope defogging and pre-heating device folded up and an endoscope received in the folded endoscope defogging and pre-heating device; FIG. 5 is a time-temperature curve, illustrating temperature changes in the endoscope at different time periods under the pre-heating operation of the endoscope defogging and pre-heating device, an endoscope defogging and pre-heating device 1 in accordance with the present invention is adapted for pre-heating an endoscope to a temperature range about 98° F.~138° F. The pre-heating device 1 comprises a bag 10, a heat storage/release material 30, a fixation device 40 and an actuator 50.

The bag 10 has a predetermined shape, for example, but not limited to, rectangular shape. According to this embodiment, the bag 10 comprises at least one, for example, but not limited to, one first seal line 11, and a first chamber 12 and a second chamber 13 defined at two opposite lateral sides relative to the first seal line 11 for accommodating the heat storage/release material 30. The first seal line 11 is longitudinally located on a middle area of the bag 10. The bag 10 is made of, but not limited to, polymeric material. Further, the bag 10 is preferably a transparent bag. For the purpose of being reusable, the material of the bag 10 has durable and extensible characteristics and a certain thickness. During fabrication, high frequency sealing technique or any other suitable sealing technique is employed to seal the periphery of the bag 10. This bag fabrication method is of the known art and not within the scope of the claims of the present invention, and therefore no further detailed description in this regard is necessary.

The bag 10 further comprises a first lug 14 and a second lug 15 respectively located at two opposite lateral sides thereof. Further, the first lug 14 and the second lug 15 are sealed to the bag 10 by high frequency sealing, thermal fusion or other bonding techniques.

The heat storage/release material 30 has the power of storing/releasing heat energy, and is accommodated in the bag 10. The heat storage/release material 30 can be pure water, saturated sodium acetate solution, or any suitable known fluid that releases heat gradually after having been heated. Further, the heat storage/release material can be stored in a refrigerator (not shown).

The fixation device 40 is mounted on the bag 10 for securing the first chamber 12 and the second chamber 13 in a stacked manner when the bag 10 is folded up. As illustrated, the fixation device 40 comprises a first fastening member 41 and a second fastening member 42. The first fastening member 41 is, for example, a male fastening member provided at the top side of the first lug 14. The second fastening member 42 is, for example, a female fastening member provided at the top side of the second lug 13 and connectable to the first fastening member 41.

The bag 10 further comprises at least one second seal line 16 disposed in the first chamber 12 at a lower side relative to the first seal line 11 so that a third chamber 17 is defined at one lateral side relative to the second seal line 16 for securing the actuator 50. Further, the heat storage/release material 30 can be selectively flowable among the first chamber 12, the second chamber 13 and the third chamber 17, or between the first chamber 12 and the third chamber 17, or between the second chamber 13 and the third chamber 17. Further, the first seal line 11 and the second seal line 16 are formed by using high frequency sealing, thermal fusion or other bonding techniques.

The actuator 50 is mounted in the third chamber 17 of the bag 10. Further, the actuator 50 is, for example, but not limited to, a metal strip that is bendable to generate oscillation waves for causing the heat storage/release material 30 to produce a temperature rise and then to release heat. With respect to this temperature rise and heat release function, please refer to the description of U.S. Pat. No. 5,205,278.

The bag 10 further comprises a plurality of recessed portions 18 located at the first chamber 12 and the second chamber 13 to reinforce the structural strength of the bag 10, enabling the heat storage/release material 30 to be evenly distributed in the first chamber 12 and the second chamber 13. Further, the recessed portions 18 can have a circular shape, or can be shaped like a slash. In this embodiment, the recessed portions 18 have a circular shape. Further, the recessed portions 18 can be formed by using high frequency technique, thermal fusion or other bonding techniques.

Referring to FIG. 4, during application of the endoscope defogging and pre-heating device 1, place the two endoscope 60 to be warmed up to the top side of the first seal line 11 of the bag 10, and then fold up the bag 10 to let the endoscope 60 be surrounded by the first chamber 12 and the second chamber 13, and then the first fastening member 41 of the first lug 14 to the second fastening member 42 of the second lug 15 to secure the endoscope 60 in the bag 10 and to keep the endoscope 60 in positive contact with the surface of the first chamber 12 and the surface of the second chamber 13, and then bend the actuator 50 with the hands, causing the actuator 50 to generate oscillation waves, and thus, the heat storage/release material 30 can be activated by the oscillation waves to produce a temperature rise and to further release heat for pre-heating the endoscope 60 to a temperature range about 98° F.~138° F. and maintaining the endoscope 60 in this temperature range. Thus, the surgeon can uses the endoscope 60 to perform an endoscopic surgery after the temperature of the endoscope 60 is dropped to about equal to or slightly above the human body temperature of 98° F., reducing patient's discomfort due to a significant temperature difference between the endoscope and the body of the patient. Thus, the endoscope defogging and pre-heating device 1 effectively achieves endoscope defogging and pre-heating effects.

In the time-temperature curve shown in FIG. 5, the X-coordinate indicates Fahrenheit temperature, and the Y-coordinate indicates heating time. In actual tests under the condition that the operating room temperature of about 68° F., the surface temperature of the endoscope 60 measured after the endoscope 60 had been pre-heated by the heat energy released by the heat storage/release material 30 of the endoscope defogging and pre-heating device 1 for one minute was about 84° F.; the surface temperature of the endoscope 60 measured the surface temperature of the endoscope 60 measured after the endoscope 60 had been pre-heated by the heat energy released by the heat storage/release material 30 of the endoscope defogging and pre-heating device 1 for two minutes was about was 100° F.; the surface temperature of the endoscope 60 measured the surface temperature of the endoscope 60 measured after the endoscope 60 had been pre-heated by the heat energy released by the heat storage/release material 30 of the endoscope defogging and pre-heating device 1 for three minutes was about was about 108° F.; the surface temperature of the endoscope 60 measured the surface temperature of the endoscope 60 measured after the endoscope 60 had been pre-heated by the heat energy released by the heat storage/release material 30 of the endoscope defogging and pre-heating device 1 for four minutes was about was about 113° F.; the surface temperature of the endoscope 60 measured the surface temperature of the endoscope 60 measured after the endoscope 60 had been pre-heated by the heat energy released by the heat storage/release material 30 of the endoscope defogging and pre-heating device 1 for five minutes was about 115° F. Thereafter, the surface temperature of the endoscope 60 was increased gradually to 138° F. Thereafter, the heat storage/release material 30 was gradually crystallized to reduce release of heat energy, causing the surface temperature of the endoscope 60 to be lowered gradually.

When the user remove the endoscope 60 from the endoscope defogging and pre-heating device 1 after the surface temperature of the endoscope 60 reached 115° F., the surface temperature of the endoscope 60 will be lowered from 115° F. to about 99° F. within few minutes, or about 5 minutes. Thus, the surgeon can use the endoscope 60 few minutes after removed it from the endoscope defogging and pre-heating device 1.

Therefore, the endoscope defogging and pre-heating device 1 of the present invention effectively eliminates the drawbacks of the prior art designs.

Figure 6:
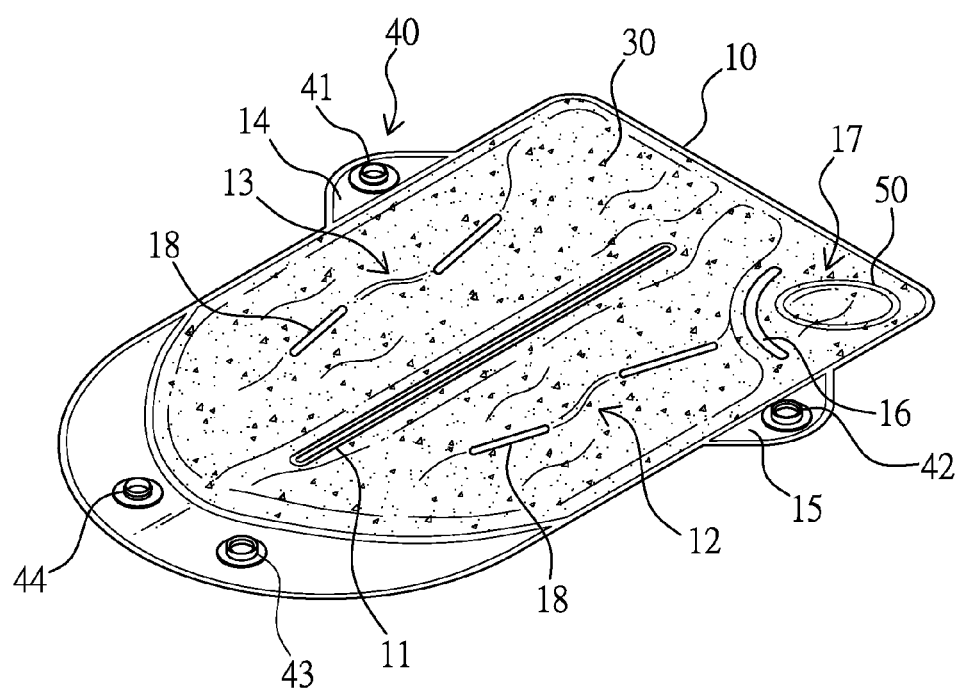
FIG. 6 is an extended view of an alternate form of the endoscope defogging and pre-heating device according to the present invention.
Figure 7:
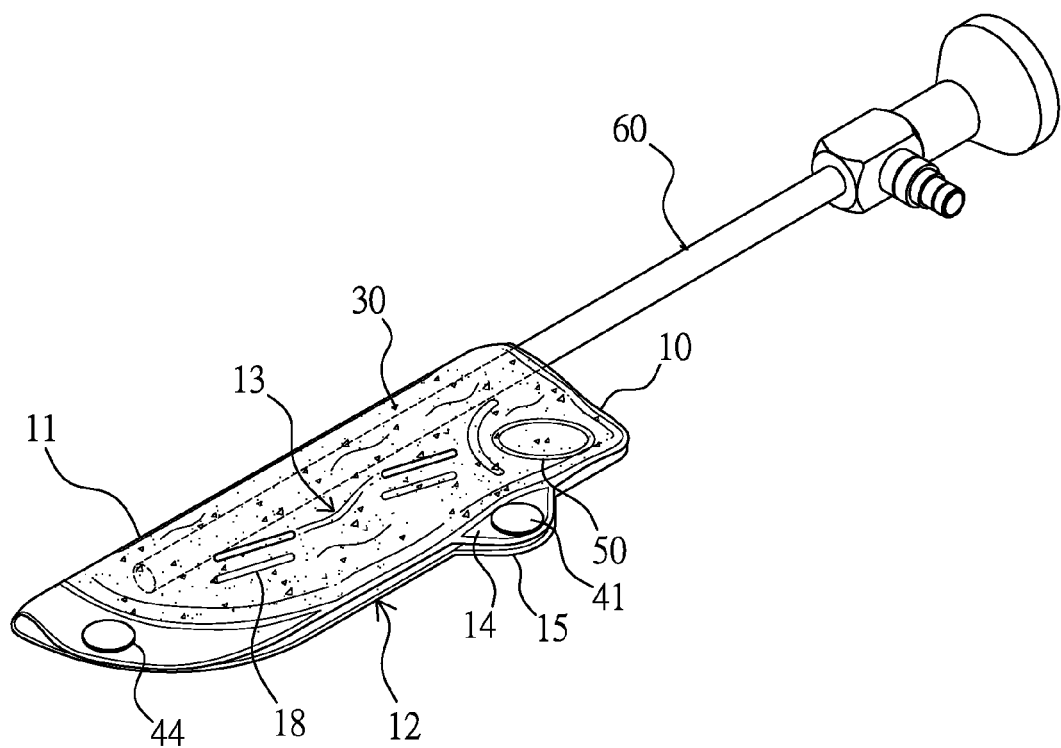
FIG. 7 is a schematic applied view of the alternate form of the present invention, illustrating the endoscope defogging and pre-heating device folded up with an endoscope set in between the first chamber and second chamber of the bag.

Referring to FIGS. 6 and 7, an alternate form of the endoscope defogging and pre-heating device 1 in accordance with the present invention is shown, wherein FIG. 6 is an extended view of an alternate form of the endoscope defogging and pre-heating device according to the present invention; FIG. 7 is a schematic applied view of the alternate form of the present invention, illustrating the endoscope defogging and pre-heating device folded up with an endoscope set in between the first chamber and second chamber of the bag.

As illustrated in FIG. 6, the fixation device 40 of the endoscope defogging and pre-heating device 1 further comprises a third fastening member 43 and a fourth fastening member 44 mounted at the bag 10. The third fastening member 43 is a male fastening member located at a center area at a top side of the first chamber 12. The fourth fastening member 44 is a female fastening member located at a center area at a top side of the second chamber 13 and fastenable to the third fastening member 43.

Referring to FIG. 7, when using this alternate form of endoscope defogging and pre-heating device 1, fasten up the first fastening member 41 and the second fastening member 42 to secure the loaded endoscope 60 in the folded bag 10, and also fasten up the third fastening member 43 and the fourth fastening member 44 to stop the head of the endoscope 60 in the folded bag 10, preventing the endoscope 60 from discharging heat.

Figure 8:
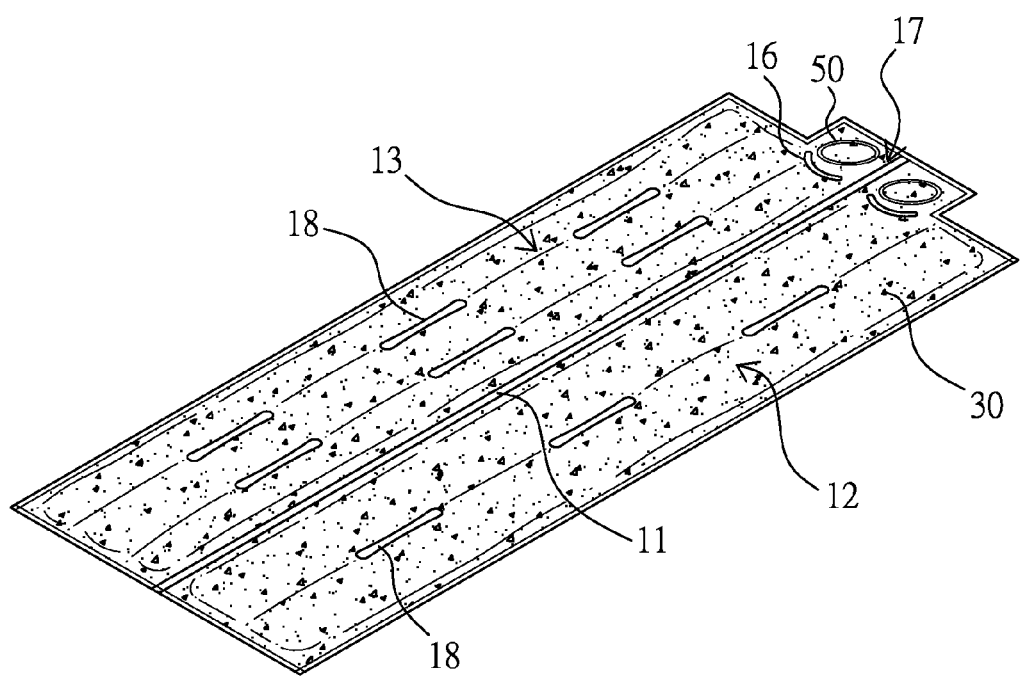
FIG. 8 is an extended view of another alternate form of the endoscope defogging and pre-heating device according to the present invention.

FIG. 8 illustrates another alternate form of endoscope defogging and pre-heating device. In this embodiment, the first chamber 12 and second chamber 13 of the bag 10 of the endoscope defogging and pre-heating device 1 are two independent chambers separated by the first seal line 11 so that the heat storage/release material 30 can simply be kept in the first chamber 12 and the second chamber 13 and prohibited from flowing between the first chamber 12 and the second chamber 13.

As stated above, the endoscope defogging and pre-heating device is provided with a fixation device that holds the bag of the endoscope defogging and pre-heating device in a folded condition to keep the endoscope to be pre-heated in positive contact with the first and second chambers of the bag for pre-heating to about 98° F.~138° F. Further, the bag of the endoscope defogging and pre-heating device has at least one first seal line and at least one second seal line to divide the inside space of the bag into a first chamber and a second chamber and a third chamber. Thus, when the bag is folded up, the endoscope to be pre-heated can be positively kept in contact with the first chamber and the second chamber and quickly pre-heated to the desired temperature range. Therefore, the invention effectively improves the drawbacks of the prior art designs.

Although particular embodiments of the invention have been described in detail for purposes of illustration, various modifications and enhancements may be made without departing from the spirit and scope of the invention. Accordingly, the invention is not to be limited except as by the appended claims.

What is claimed is:

1. An endoscope defogging and pre-heating device for pre-heating endoscopes, comprising:

a bag comprising at least one first seal line, a first chamber defined at one lateral side relative to said at least one first seal line and a second chamber defined at an opposite lateral side relative to said at least one first seal line;

a heat storage/release material accommodated in said bag and flowing in said first chamber and said second chamber and adapted for storing/releasing heat energy;

a fixation device mounted at two opposite lateral sides of said bag and adapted for securing said bag in a folded status for surrounding an endoscope with said first chamber and said second chamber; and an actuator mounted in said bag and bendable to generate oscillation waves for causing said heat storage/release material to produce a temperature rise and then to release heat for pre-heating an endoscope to a temperature range about 98° F.~138° F.;

wherein said bag further comprises a first lug and a second lug respectively located at two opposite lateral sides thereof;

wherein said fixation device comprises a first fastening member located at said first lug, and a second fastening member located at said second lug and fastenable to said first fastening member.

2. The endoscope defogging and pre-heating device as claimed in claim 1, wherein said heat storage/release material is saturated sodium acetate solution.

3. The endoscope defogging and pre-heating device as claimed in claim 1, wherein said bag is made of a polymeric material.

4. The endoscope defogging and pre-heating device as claimed in claim 1, wherein said first fastening member is a male fastening member, and, said second fastening member is a female fastening member.

5. The endoscope defogging and pre-heating device as claimed in claim 1, wherein said at least one first seal line is longitudinally disposed in a middle area of said bag.

6. The endoscope defogging and pre-heating device as claimed in claim 1, wherein said bag further comprises a second seal line located at one of said first chamber and said second chamber at a lower side relative to said first seal line, and a third chamber defined at one lateral side relative to said second seal line for securing said actuator; said heat storage/release material is selectively flowable among said first chamber, said second chamber and said third chamber, or between said first chamber and said third chamber, or between said second chamber and said third chamber.

7. The endoscope defogging and pre-heating device as claimed in claim 6, wherein said at least one first seal line, said second seal line, said first lug and said second lug are formed on said bag by one of high frequency and thermal fusion techniques.

8. The endoscope defogging and pre-heating device as claimed in claim 1, wherein said fixation device further comprises a third fastening member located at said bag at a top side of said first chamber, and a fourth fastening member located at said bag at a top side of said second chamber and fastenable to said third fastening member.

9. The endoscope defogging and pre-heating device as claimed in claim 8, wherein said third fastening member is a male fastening member, and, said fourth fastening member is a female fastening member.

10. The endoscope defogging and pre-heating device as claimed in claim 1, wherein said bag further comprises a plurality of at least one recessed portion located at each of said first chamber and said second chamber to reinforce the structural strength of said bag and for enabling said heat storage/release material to be evenly distributed in said first chamber and said second chamber.

\* \* \* \* \*